US006245513B1

(12) United States Patent
Lane et al.

(10) Patent No.: US 6,245,513 B1
(45) Date of Patent: *Jun. 12, 2001

(54) SIGNAL AMPLIFICATION METHOD

(75) Inventors: Michael J. Lane, Baldwinsville, NY (US); Albert S. Benight, Schaumburg, IL (US); Brian D. Faldasz, Maynard, MA (US)

(73) Assignee: Tm Technologies, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/293,362

(22) Filed: Apr. 16, 1999

Related U.S. Application Data

(63) Continuation of application No. 08/893,535, filed on Jul. 11, 1997, now Pat. No. 5,902,724.
(60) Provisional application No. 60/022,718, filed on Jul. 12, 1996.

(51) Int. Cl.$^7$ .............................. C12N 15/00; C12Q 1/68
(52) U.S. Cl. ..................... 435/6; 536/23.1; 536/24.3; 536/24.33; 536/25.3; 536/25.4; 536/25.5
(58) Field of Search .................................. 435/6; 536/23.1, 536/24.3, 24.33, 25.3, 25.4, 25.5

(56) References Cited

U.S. PATENT DOCUMENTS

| 4,716,106 | 12/1987 | Chiswell ................................ 435/6 |
| 4,882,269 | 11/1989 | Schneider et al. ...................... 435/6 |
| 4,994,373 | 2/1991 | Stavrianopoulos et al. ............. 435/6 |
| 5,124,246 | * 6/1992 | Urdea et al. ............................ 435/6 |
| 5,424,188 | 6/1995 | Schneider et al. ...................... 435/6 |
| 5,437,977 | 8/1995 | Segev ...................................... 435/6 |
| 5,567,591 | 10/1996 | Lovell et al. ......................... 435/7.5 |
| 5,627,030 | 5/1997 | Pandian et al. ......................... 435/6 |
| 5,635,352 | 6/1997 | Urdea et al. ............................ 435/6 |
| 5,681,702 | * 8/1994 | Collins et al. ......................... 435/6 |

FOREIGN PATENT DOCUMENTS

| 0128332 | 5/1984 | (EP) . |
| 0204510 | 12/1986 | (EP) . |
| WO 8403520 | 9/1984 | (WO) . |
| WO 8703622 | 6/1987 | (WO) . |
| WO 9600795 | 1/1996 | (WO) . |
| WO 9708183 | 3/1997 | (WO) . |

* cited by examiner

Primary Examiner—Robert A. Schwartzman
Assistant Examiner—M Schmidt
(74) Attorney, Agent, or Firm—Lahive & Cockfield, LLP; Giulio A. DeConti, Jr., Esq.; Nicholas P. Triano, III, Esq.

(57) ABSTRACT

Methods for detecting the presence or absence of an analyte in a sample are disclosed. Kits for performing the analysis methods of the invention are also disclosed.

31 Claims, 5 Drawing Sheets

SEQUENCE LISTING

<160> NUMBER OF SEQ ID NOS: 3

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence:Synthetic
      Target Molecule

<400> SEQUENCE: 1
aacaagcggc taggagttcc gcagtatgga tcggcagagg agcc                44

<210> SEQ ID NO 2
<211> LENGTH: 57
<212> TYPE: DNA
<213> ORGANISM: Artificial Sequence -continued

```
<220> FEATURE:
<223> OTHER INFORMATION: AT POSITION 19 N=BIOTINYLATED URACIL
<220> FEATURE:
<223> OTHER INFORMATION: Description of Artificial Sequence:Hair Pin
      Probe

<400> SEQUENCE: 2
ctagtcgacg tggtccttnt tggaccacgt cgactagggc tcctctgccg atccata        57

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:Probe

<400> SEQUENCE: 3
ctgcggaact cctagccgct tgttttttttt tttttttttt tttt                     44
```

SIGNAL AMPLIFICATION METHOD

RELATED APPLICATIONS

This application is a continuation application of Ser. No. 08/893,535 filed on Jul. 11, 1997, now U.S. Pat. No. 5,902,724. The contents of all the aforementioned application(s) are hereby incorporated by reference.

This application claims the benefit of priority under 35 U.S.C. 119(e) to co-pending U.S. provisional application Ser. No. 60/022,718, filed Jul. 12, 1996, the entire content of which is hereby incorporated by reference.

BACKGROUND OF THE INVENTION

Biochemical assays such as immunoassays (e.g., enzyme-linked immunosorbent assay (ELISA)) and methods for detecting nucleic acid sequences in a test sample are well known. In such assays, high sensitivity is important to ensuring the ability of the assay to detect low levels of the analyte of interest. Radioactive and colorimetric methods have often been employed in such assays. However, achieving high levels of sensitivity has not always been possible, and methods of increasing the sensitivity of such tests are desirable.

One reported method (European Patent Publication EP 128 332) for detecting analytes, including nucleic acid sequences and antigens (or antibodies), is the use of a "bridging moiety," which provides a bridge between an analyte and a "signalling moiety" which provides a detectable signal. The bridging moiety includes an analyte-specific region and a signalling moiety-specific region. This method has the advantage that, by varying the bridging moiety according to the target analyte, the same signalling moiety can be employed to detect a variety of analytes. However, the preparation of the bridging moieties can be rather lengthy and inefficient. Also, large bridging moieties (such a long polynucleotide sequences) may be less sensitive at detecting target analyte due to the presence of large segments which do not bind to the target. Moreover, this method requires that the analyte-specific region and a signalling moiety-specific region of the bridging moiety be different.

Another publication (U.S. Pat. No. 5,627,030 to Pandian et al.) describes the use of a primary probe for detecting a target nucleic acid sequence, and an "amplification probe", which is a nucleic acid sequence which includes two regions: a first region complementary to the primary probe, and a second region which contains repeated sequences for binding to a plurality of labeled probes. The amplification probe permits several labeled probes to bind to each primary probe, amplifying the signal from the binding of the primary probe to the target molecule in the sample. However, construction of the amplification probe can be cumbersome.

SUMMARY OF THE INVENTION

The present invention relates to methods and compositions for amplifying or amplifying signals in biochemical assays. In particular, the invention provides methods and compositions useful for improving sensitivity in biochemical assays involving the binding of specific binding pairs.

In one aspect, the invention provides amplifying entities (also referred to herein as polymeric amplifying moieties (PAMs)) which are capable of binding to both an analyte (e.g., an antigen or nucleic acid) or analyte-detecting moiety (e.g., an antibody, a nucleic acid probe, and the like) and to a plurality of signalling moieties which include a detectable label. By binding to multiple signalling moieties, the PAM amplifies the signal generated in the presence of the analyte, thereby detecting the presence or absence of the analyte in a sample.

In another aspect, the invention provides a method for amplifying signals in assay systems. The method includes the steps of contacting the sample with a reagent having a first portion which specifically binds to the analyte and a second portion comprising a polynucleotide sequence, such that a complex of the analyte and the reagent is formed; contacting the complex of the analyte and the reagent with an amplifying entity having a first polynucleotide sequence and a second polynucleotide sequence, wherein the first polynucleotide sequence is complementary to the polynucleotide sequence of the second portion of the reagent, such that a complex of the analyte, the reagent, and the amplifying entity is formed; contacting the complex of the analyte, the reagent, and the amplifying entity with a plurality of signalling moieties, each of the signalling moieties comprising a detectable label and a polynucleotide sequence complementary to the second polynucleotide sequence of the amplifying entity, to form a detectable complex of the analyte, the reagent, the amplifying polynucleotide and the signalling moieties; and detecting the label as indicative of the presence or absence of analyte in the sample.

The analyte can be a nucleic acid sequence; the reagent first portion can be a nucleic acid sequence which is substantially complementary to the analyte; the analyte can be an antibody or antigen; the reagent first portion can be an antibody or antigen which specifically binds with the analyte; the amplifying entity first polynucleotide sequence and second polynucleotide sequence comprise the same or substantially the same sequence. In certain embodiments, the amplifying entity is a homopolynucleotide; the homopolynucleotide can comprise poly(dA); the poly(dA) can have a length of at least about 3000 bases; the reagent second portion can comprise poly(dT); each of the signalling moieties comprises poly(dT); each of the signalling moieties can comprise a detectable label selected from the group consisting of antigens, antibodies, enzymes, radioisotopes, and fluorescent moieties. In certain embodiments, prior to the step of contacting the complex of the analyte, the reagent and the amplifying entity with the plurality of signalling moieties, the method comprises the further step of washing the complex of the analyte, the reagent and the amplifying entity to remove unbound polynucleotide. In preferred embodiments, the analyte is immobilized with an immobilized capture reagent.

In another embodiment, the invention provides a method for detecting the presence or absence of an analyte in a sample, the method including the steps of contacting the sample with a reagent having a first portion which specifically binds to the analyte and a second portion comprising a homopolynucleotide sequence, such that a complex of the analyte and the reagent is formed; contacting the complex of the analyte and the reagent with a homopolynucleotide strand complementary to the homopolynucleotide sequence of the reagent, such that a complex of the analyte, the reagent, and the homopolynucleotide is formed; and contacting the complex of the analyte, the reagent, and the homopolynucleotide with a plurality of signalling moieties, each of the signalling moieties comprising a detectable label and a homopolynucleotide sequence complementary to homopolynucleotide strand, to form a detectable complex of the analyte, the reagent, the homopolynucleotide strand and the signalling moieties; and detecting the label as indicative of the presence or absence of analyte in the sample.

In certain embodiments, the homopolynucleotide strand is poly(da) and the reagent second portion and the signalling moieties comprise poly(dT) or poly(dU).

In still another aspect, the invention provides a method for detecting the presence or absence of an analyte in a sample, the method comprising the steps of contacting the sample with a first reagent having a first portion which specifically binds to the analyte and a second portion comprising a polynucleotide sequence, such that a complex of the analyte and the first reagent is formed; contacting the complex of the analyte and the first reagent with an amplifying entity having a first polynucleotide sequence and a second polynucleotide sequence, wherein the first polynucleotide sequence is complementary to the polynucleotide sequence of the second portion of the first reagent, such that a complex of the analyte, the first reagent, and the amplifying entity is formed; contacting the complex of the analyte, the first reagent, and the amplifying entity with a second reagent, the second reagent having a first portion which includes a polynucleotide sequence complementary to the second polynucleotide sequence of the amplifying entity, and a second portion, to form an extendable complex of the analyte, the first reagent, the amplifying entity and the second reagent; contacting the extendable complex with an extension reagent, the extension reagent comprising a first portion capable of specifically binding to the second portion of the amplifying entity, and a second portion which comprises a polynucleotide sequence, such that the extension reagent binds to the extendable complex to form a complex of the analyte, the first reagent, the amplifying entity, and the extension reagent; and contacting the complex of the analyte, the first reagent, the amplifying entity and the extension reagent with a plurality of signalling moieties, each of the signalling moieties comprising a detectable label and a polynucleotide sequence complementary to the polynucleotide sequence of the extension reagent, to form a detectable complex of the analyte, the reagent, the amplifying polynucleotide, the extension reagent and the signalling moieties; and detecting the label as indicative of the presence or absence of analyte in the sample.

In certain embodiments, the second portion of the extension reagent comprises a homopolynucleotide; the second portion of the extension reagent comprises poly(dC), and the polynucleotide sequence of the signalling moieties comprises poly(dG); the detectable label is selected from the group consisting of antigens, antibodies, enzymes, radioisotopes, and fluorescent moieties.

In another aspect, the invention provides a kit for detecting the presence or absence of an analyte in a sample. The kit includes a container including a reagent having a first portion which specifically binds to the analyte and a second portion comprising a polynucleotide sequence; a container including an amplifying entity having a first polynucleotide sequence and a second polynucleotide sequence, wherein the first polynucleotide sequence is complementary to the polynucleotide sequence of the second portion of the reagent; a container including a plurality of signalling moieties, each of the signalling moieties comprising a detectable label and a polynucleotide sequence complementary to the second polynucleotide sequence of the amplifying entity; and instructions for detecting the presence or absence of the analyte in a sample.

In preferred embodiments, the amplifying entity is a homopolynucleotide; the homopolynucleotide can comprise poly(dA); the poly(dA) can have a length of at least about 3000 bases; the reagent second portion can comprise poly(dT). In certain embodiments, the kit further includes a container of an analyte-specific capture reagent; analyte-specific capture reagent can be immobilized on a solid support.

In another aspect, the invention provides a detectable complex for detection of an analyte, the complex comprising a reagent bound to an analyte, the reagent having a first portion which specifically binds to the analyte and a second portion comprising a polynucleotide sequence; an amplifying entity bound to the reagent, the amplifying entity having a first polynucleotide sequence and a second polynucleotide sequence, wherein the first polynucleotide sequence is complementary to the polynucleotide sequence of the second portion of the reagent; and a plurality of signalling moieties bound to the amplifying entity, each of the signalling moieties comprising a detectable label and a polynucleotide sequence complementary to the second polynucleotide sequence of the amplifying entity. The detectable complex can further include an analyte-specific capture reagent bound to a solid support, the capture reagent further being bound to the analyte. In preferred embodiments, the analyte can be an antigen or nucleic acid.

In still another aspect, the invention provides an isolated purified single-stranded homopolynucleotide having a length of at least about 3000 bases, more preferably a length of at least about 7000 bases. In preferred embodiments, the homopolynucleotide is selected from the group consisting of poly(dA), poly(dT), poly(dC), poly(dG), and poly(dU).

In the methods and compositions of the invention, the PAM can bind to the analyte-detecting moiety and to a plurality of signalling moieties. The present invention is based, at least in part, on the discovery that the portions of the PAM which recognize the analyte-detecting moiety and the signalling moieties can be the same. This finding permits simplified synthesis and use of the PAMs, thus reducing the time and cost required to provide suitable assay systems. Furthermore, the simplified PAMs of the invention can be constructed to permit the binding of greater numbers of signalling moieties than heretofore contemplated.

DETAILED DESCRIPTION OF THE INVENTION

Figure 1:
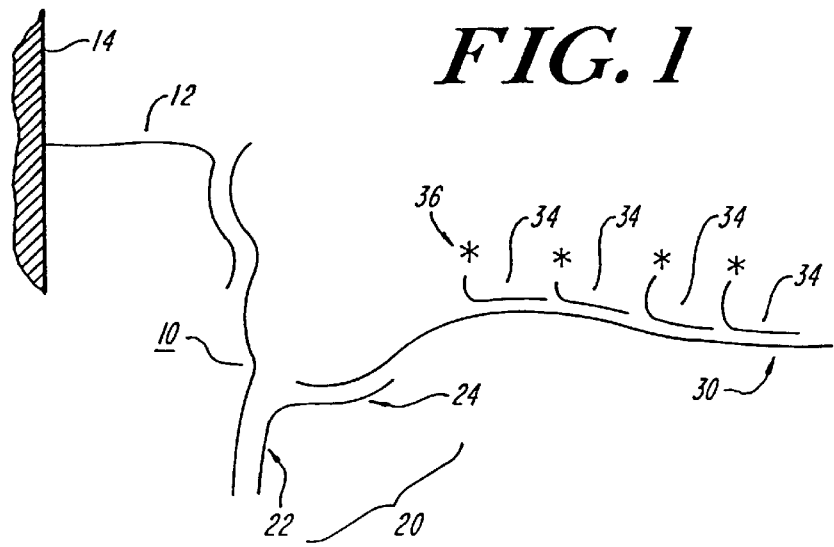
FIG. 1 depicts a generalized scheme for detection of an analyte according to the methods of the invention.

The present invention provides methods and compositions for amplification of signals in binding assays.

The methods and compositions of the invention are useful in assays in which an analyte, which is a member of a specific binding pair, is detected by binding of the other member of the specific-binding pair. Specific binding pairs are known in the art and include pairs such as antibody-antigen, hormone-receptor, binding ligand-substrate, lectin-sugar, enzyme-inhibitor, and the like. The term "detecting" as used herein, can include determination of the presence or absence of an analyte in a sample, and/or quantitation of the amount of analyte in the sample.

The amplifying entity (or polymeric amplifying moiety (PAM)) of the invention can be any moiety capable of binding to (i) an analyte or analyte-binding moiety and (ii) a plurality of signalling moieties. For example, in a preferred embodiment, a PAM is a polynucleotide, more preferably a homopolynucleotide, preferably poly(A) or, more preferably, poly(dA). Poly(dA) can bind to a complementary sequence of an analyte or analyte-binding moiety, and to a complementary sequence of a plurality of signalling moieties. For example, poly(da) can bind to a sequence comprising poly(dT), poly(dU), or a sequence comprising a polymer of dT and dU. In other embodiments, the PAM can be a polysaccharide, a polypeptide, or other polymer capable of binding to an analyte or analyte-binding moiety and to multiple signalling moieties. A PAM can also be a hybrid molecule, e.g., a protein-nucleic acid conjugate, and the like.

The signalling moiety can be any molecular entity which can bind to the amplifying entity and comprises a portion that can generate a signal, or which can bind to or interact with a moiety that can generate a signal. Suitable signalling moieties can be prepared according to methods known in the art, and can be prepared to bind to a pre-selected amplifying entity. The signalling moiety can comprise a detectable label. The label, if present, can be, e.g., a radionuclide, an enzyme (such as alkaline phosphatase (AP) or horse radish peroxidase (HRP)), an antibody, an antigen (such as FITC), a member of a specific binding pair (such as biotin/streptavidin), a fluorescent moiety, a dye, and the like. In an exemplary embodiment, if the amplifying entity is poly(dA), a suitable signalling moiety would be labelled poly(dT), e.g., FITC-dT$_{15}$ (FITC=fluorescein isothiocyanate). In this illustrative embodiment, the poly(dT) portion of the signalling moiety can bind to an amplifying entity such as poly(dA), while the FITC portion of the signalling moiety can bind to, e.g., an anti-FITC/allaline phosphatase conjugate. The anti-FITC/alkaline phosphatase conjugate can generate a colorimetric signal by reaction with an appropriate substrate for the enzyme, as is conventional in the art.

A plurality of signalling moieties are used to bind to each PAM; the signalling moieties can be the same or may be different. For example, if the PAM is poly(da) a plurality of, e.g., FITC-dT$_{15}$ moieties can be used to bind to each strand of poly(dA), and the signal detected by use of an anti-FITC-alkaline phosphatase conjugate, which can react with a substrate to produce a colored product. Alternatively, a FITC-dT1$_5$ signalling moiety could be used together with a $^{32}$P-dT$_{15}$ moiety. Both signalling moieties could then bind to the poly(da) strand to provide both colorimetric and radioactive detection modes.

A preferred PAM is a single-stranded polynucleotide sequence which includes at least two non-overlapping occurrences of a nucleic acid sequence (each occurrence is referred to herein as a "subsequence"). A polynucleotide having at least two non-overlapping occurrences of a nucleic acid sequence is referred to herein as a "repeating polynucleotide" (RP). It will be appreciated that a subsequence can itself include repeated units or can be a homopolynucleotide sequence. An RP can include DNA, RNA, mixtures of DNA and RNA, or nucleic acid analogs or congeners including phosphorothioates and peptide nucleic acid (PNA). An RP can have two occurrences of a nucleic acid sequence (the subsequence), but more preferably includes at least 3, 5, 10, 15, 20, 30, 50, 100, 200, 300, 500, 700, 1000, 2000, 5000, or 10,000 non-overlapping occurrences of a subsequence. In preferred embodiments, an RP has a total length of at least about 30 bases, more preferably at least about 50 bases, more preferably at least about 100 bases, more preferably at least about 500 bases, more preferably at least about 1000 bases, and most preferably at least about 5000 bases. In certain embodiments, an RP has a length less than about 10,000 bases, less than about 5000 bases, less than about 1000 bases, or less than about 500 bases.

Complementary polynucleotide sequences should be long enough to permit stable hybridization under stringency conditions associated with washing, detection, and the like, e.g., binding of a subsequence to its complement should not be substantially disrupted by normal washing conditions and the like. For example, the polynucleotide sequence of the reagent second portion should be long enough to stably hybridize to the first polynucleotide sequence of the amplification entity under washing conditions, and the polynucleotide sequence of the signalling moiety which is complementary to the amplifying entity second polynucleotide sequence should be long enough to stably hybridize to the second polynucleotide sequence of the amplification entity. Thus, in preferred embodiments, a subsequence is at least about 6 bases in length, more preferably at least about 10 bases in length, at least about 15 bases in length, at least about 20 bases in length, at least about 25 bases in length, at least about 30 bases in length, at least about 50 bases in length, or at least about 100 bases in length. In a preferred embodiment, an amplifying entity is a linear (not circular) polynucleotide sequence.

An RP can include "contiguous" subsequences (in which two or more subsequences are contiguous with each other), "non-contiguous" subsequences (in which at least one base intervenes between subsequences), or a combination of contiguous and non-contiguous subsequences. For example, if a subsequence (which is at least six bases in length) is represented as X, an RP including the subsequence could be represented as follows: X-Y-X-X-Z-X, in which Y and Z are bases or sequences which do not include subsequence X. This exemplary RP includes both contiguous subsequences (illustrated as X-X) and non-contiguous subsequences (such as X-Z-X, in which the sequence portion Z separates two subsequences). In certain embodiments, contiguous subsequences are preferred, because there are fewer extraneous bases in the RP. In a particularly preferred embodiment, the RP comprises contiguous subsequences, with substantially no non-contiguous subsequences or non-subsequence regions.

Subsequences can be selected according to factors such as the ease of preparation of the RP, ease of preparation of a complement to the subsequence (for example, a labelled signalling moiety or probe), and the like. An RP preferably does not include self-complementary regions which could form secondary structures such as loops; such secondary structure formation could interfere with the ability of the RP to hybridize to the analyte or to the signalling moiety. It will be understood that an RP can include more than one sequence which is repeated (i.e., can include more than one type of subsequence). Thus, an RP could have the structure X-Y-X-Y-X-Y, in which X and Y are different nucleic acid subsequences.

It will be understood from the discussion herein that a preferred amplifying entity includes a first polynucleotide sequence complementary to a polynucleotide portion of an analyte-specific reagent, and a second polynucleotide sequence which is complementary to a polynucleotide portion of a signalling moiety. In a particularly preferred embodiment, the first and second polynucleotide sequences of the amplifying entity comprise the same or substantially the same sequence. In a preferred embodiment, each of the first and second polynucleotide sequences of the amplifying entity have a length of at least about 6 bases, more preferably at least about 12 bases, 15 bases, 20 bases, 25 bases, or 35 bases. This result can be obtained by using a homopolynucleotide as the amplifying entity. A homopolynucleotide can be viewed as including two portions, C and D, both including the same homopolynucleotide sequence. Thus, a particularly preferred amplifying moiety is a homopolynucleotide sequence, i.e., a nucleotide sequence composed of a single nucleotide base N; a homopolynucleotide having n bases is designated $N_n$, in which n is an integer in the range of 6 to 10,000, inclusive. It will be appreciated that a homopolynucleotide of length 100 includes 2 subsequences of length 50, 4 subsequences of length 25, etc. Other homopolynucleotide sequences will similarly include homopolynucleotide subsequences. Thus, a homopolynucleotide provides an efficient amplifying entity, due to the availability of multiple subsequences (for bonding to a plurality of signalling moieties) without extraneous bases which do not bind to signalling moiety or analyte.

As described in detail below, an amplifying entity which comprises a homopolynucleotide can be obtained commercially and/or readily prepared in the laboratory. Preferred amplifying entities include $dA_n$, $dT_n$, $dC_n$, $dG_n$, $dU_n$ in which dA, dT, dC, dG and dU represent deoxyadenosine, deoxythymidine, deoxycytosine, deoxyguanine, and deoxyuracil, respectively, and n is an integer greater than 100, preferably greater than 500, more preferably at least about 1000, more preferably at least about 3000, more preferably at least about 5000, more preferably at least about 7000, and still more preferably greater than 9000.

According to the present invention, the PAM (e.g., an amplifying entity such as a homopolynucleotide) and the signalling moiety are selected such that at least two signalling moieties can bind to each strand of PAM, e.g., after washing to remove i) PAM which is not complexed to an analyte molecule (directly or through a analyte-specific reagent) and/or ii) unbound signalling moieties. In preferred embodiments, the number of signalling moieties bound to each strand of amplifying entity is at least about 5, more preferably at least about 10, more preferably at least about 20, 50, 100, 200, 300, 500, 1000 or 2000.

Without wishing to be bound by theory, it is believed that the ability of a nucleic acid to bind to its complementary sequence can be affected by the size of the nucleic acid strand. It is further believed that such effects can reduce the sensitivity of conventional nucleic acid probes which include long segments not complementary to the target (analyte) sequence. It is believed that such non-complementary sequences can decrease the ability of a probe to sensitively and selectively bind to its target. The present invention provides amplification systems in which the ability of an analyte-binding reagent to bind to an analyte is not significantly impaired by the PAM. Thus, the methods of the invention retain high analyte specificity and sensitivity while providing significant amplification of a generated signal.

I. Methods

In one aspect, the invention provides a method for detecting the presence or absence of an analyte in a sample. The analyte can be, e.g., a nucleic acid sequence (such as a DNA sequence or RNA sequence) or a member of a specific binding pair such as antibody/antigen, hormone/receptor, and the like. The sample can be, inter alia, a biological sample such as a tissue biopsy or a sample of a biological fluid such as blood, urine, semen, saliva, and the like.

In general, the methods of the invention include the steps of contacting the sample with a reagent having a first portion which specifically binds to the analyte and a second portion comprising a polynucleotide sequence, such that a complex of the analyte and the reagent is formed; contacting the complex of the analyte and the reagent with an amplifying entity having a first polynucleotide sequence and a second polynucleotide sequence, wherein the first polynucleotide sequence is complementary to the polynucleotide sequence of the second portion of the reagent, such that a complex of the analyte, the reagent, and the amplifying entity is formed; contacting the complex of the analyte, the reagent, and the amplifying entity with a plurality of signalling moieties, each of the signalling moieties comprising a detectable label and a polynucleotide sequence complementary to the second polynucleotide sequence of the amplifying entity, to form a detectable complex of the analyte, the reagent, the amplifying polynucleotide and the signalling moieties; and detecting the label as indicative of the presence or absence of analyte in the sample. This embodiment is illustrated in FIG. 1. As shown in FIG. 1, an analyte 10 (depicted as a nucleic acid in FIG. 1, which can be immobilized with a capture reagent 12 (such as a complementary probe) bound to a solid support 14) is contacted with reagent 20, which includes an analyte-binding first portion 22 and a second portion 24 which includes a polynucleotide sequence complementary to a first polynucleotide sequence of an amplifying entity 30. The amplifying entity includes a first polynucleotide sequence which is complementary to the polynucleotide sequence of the second portion of the reagent, and a second polynucleotide sequence. A plurality of signalling moieties 34 (including detectable label portion 36) and a polynucleotide sequence complementary to the second polynucleotide sequence of the amplifying entity 30 to provide a signal which indicates the presence of analyte 10 in the sample.

The reagent is selected to have a first portion capable of binding selectively to the analyte. If the analyte is a nucleic acid, this selective binding portion can be, e.g., a nucleic acid sequence complementary to at least a portion of the analyte; a nucleic acid binding protein which selectively binds to the analyte sequence; an antibody which selectively binds to the analyte nucleic acid sequence; and the like. If the analyte is, e.g., an antigen, the first portion of the reagent can be an antibody which binds to the antigen. If the analyte is an antibody, the first portion of the reagent can be an antigen to which the antibody binds, or the first portion of the reagent can be an anti-analyte antibody. If the analyte is a hormone, the first portion of the reagent can be a receptor for the hormone. Other examples of selective binding portions of the reagent will be apparent to the ordinarily skilled artisan.

The selective binding first portion of the reagent is covalently bonded to a second portion which is includes a polynucleotide sequence complementary to a polynucleotide sequence of an amplifying entity. The second portion can be readily prepared to be complementary to an amplifying entity, e.g., by convention chemical or biochemical nucleotide synthesis. Methods for covalently linking an first portion of a reagent with a second portion of the reagent are also routine to one of ordinary skill in the art. For example, a protein (such as an antibody) can be linked to a nucleic acid through use of a bifunctional linking reagent (see, e.g., Example 3, infra). Similarly, a nucleic acid (which is complementary to a nucleic acid analyte) can be covalently bonded to a nucleic acid which is complementary to the amplifying entity by conventional chemical or biochemical methods. For example, an analyte-specific probe (A) can first be synthesized, a polynucleotide sequence (B) complementary to the amplifying entity can then be synthesized, and then the A portion ligated to the B portion (e.g., by chemical synthesis or ligation with an enzyme such as ligase) to form the reagent. Alternatively, the reagent could be synthesized as a single strand, e.g., using an automated nucleotide synthesizer. It will be appreciated that the reagent can have a plurality of portions which are complementary to the amplifying entity (i.e., can be represented by the formula A-(B)$_n$, in which A is the first portion, B is a polynucleotide sequence complementary to the amplifying entity, and n is an integer greater than one). For example, the antibody-nucleic acid conjugate reagents prepared in Example 3, infra, may have more than one nucleic acid "tail" per antibody portion. Such a reagent can provide additional signal enhancement by binding to a plurality of amplifying entities, thus providing additional binding sites for signalling moieties.

The analyte-binding reagent will in general be contacted with the analyte under conditions such that an analyte:reagent complex can form. Thus, for example, appropriate conditions of stringency will be employed to ensure hybridization to a nucleic acid analyte, and conditions suitable for binding of an antibody to an antigen will be employed where the analyte is an antigen. If desired, the analyte:reagent complex can be washed to remove impurities, such as impurities and other components of the sample, extra reagents, and the like. If a washing step is employed, care should be taken to ensure that the conditions of the wash do not cause substantial dissociation of the analyte:reagent complex.

In certain embodiments, it is preferred that the analyte be immobilized to a solid support to facilitate the washing process. Thus, for example, a nucleic acid analyte can be immobilized on a nitrocellulose filter, or can be immobilized by hybridization to an immobilized capture moiety, such as the hairpin capture moieties described in PCT Publication No. PCT/US96/13546. A hairpin capture moiety can be selected so that the capture moiety binds to (is complementary to) a region of the target nucleic acid sequence which is contiguous with the region of the target sequence to which the analyte-specific reagent is bound (where the reagent first is a target-complementary sequence). This arrangement has the advantage that the binding of the reagent to the hairpin-bound target will result in a base-stacking interaction between the hairpin and the first portion polynucleotide sequence of the reagent, which can provide additional mismatch discrimination. If the analyte is an antigen, it can be immobilized by methods known in the art. For example, an immobilized antibody (bound to a solid support) which binds to the antigen can be employed to immobilize the antigen.

Once the analyte:reagent complex is formed (and, optionally, washed to remove impurities), the analyte:reagent complex is contacted with an amplifying entity such that an analyte:reagent:amplifying entity complex is formed. As described above, the contacting step should occur under such conditions, and for sufficient time, to ensure that an analyte:reagent:amplifying entity complex is formed, i.e., the appropriate conditions of stringency will be employed to ensure hybridization of the analyte:reagent complex to the amplifying entity. Once the analyte:reagent:amplifying entity complex has formed, it is preferably washed to remove impurities, excess reagents, and the like, as described above.

The method includes the further step of contacting the analyte:reagent:amplifying entity complex with a plurality of detectably-labeled RP-complementary signalling moieties to form a detectable complex, such that the presence or absence of analyte in the sample is detected. The term "detectable complex" refers to a complex of an analyte, a reagent as described above, an amplifying entity, and a detectably-labelled signalling moiety. The signalling moiety includes a polynucleotide sequence which is complementary to the second polynucleotide sequence of the amplifying entity. A detectably-labelled moiety can be detected either directly or indirectly. For example, a radioisotope is a detectable label, which can be detected, e.g., by scintillation counting or with X-ray film, and the like. Other detectable labels include, e.g., the labels described above. A "plurality" of signalling moieties can include more than one occurrence of a single signalling moiety, or can include multiple different signalling moieties. For example, an amplifying entity having the structure X-Y-X-Y-X-Y (in which X and Y are different sequences) could be contacted with a plurality of signalling moieties of the formula $X_c^*$, in which $X_c$ represents a sequence complementary to X, and * represents a detectable label; or the RP could be contacted with a plurality of signalling moieties of the formula $Y_c^*$, in which $Y_c$ represents a sequence complementary to Y, and * represents a detectable label; or the RP could be contacted with a plurality of signalling moieties including a mixture of $X_c^*$ and $Y_c^*$.

As described herein, the detectable complex (if such has formed due to the presence of analyte in the sample) can be detected by detection of the label on the signalling moieties. In a preferred embodiment, the detectable complex is washed to remove impurities, unbound signalling moieties, and the like, to reduce background noise in the detection process.

In a preferred embodiment, the amplifying entity is poly (dA), and each of the signalling moieties comprises poly (dT) or poly(dU), preferably $dT_m$ or $dU_m$, in which m is an integer in the range of 15 to 35, more preferably about 25. In this embodiment, the analyte-binding reagent second portion preferably includes a poly(dT) "tail" to which the poly(da) amplifying entity can bind.

It will be appreciated by the skilled artisan that the presence of multiple signalling moieties bound to the analyte:reagent:amplifying entity complex (due to multiple signalling-moiety binding sites of the amplifying entity) can provide an amplified signal compared to methods in which only a single signal moiety (or detectable label) is bound to each analyte molecule. Thus, the methods of the invention provide amplified signal compared to many conventional methods. In preferred embodiments, the signal, or the signal-to-noise ratio, is enhanced by at least about a factor of two, more preferably by a factor of at least about 5, 10, 20, 50, 100, 200, 500, or 1000. In preferred embodiments, the methods of the invention provide methods which are at least 2, 5, 10, 50, 100, 500, 1000, or 5000-fold more sensitive than non-amplified assays using the same detectable label.

Figure 2:
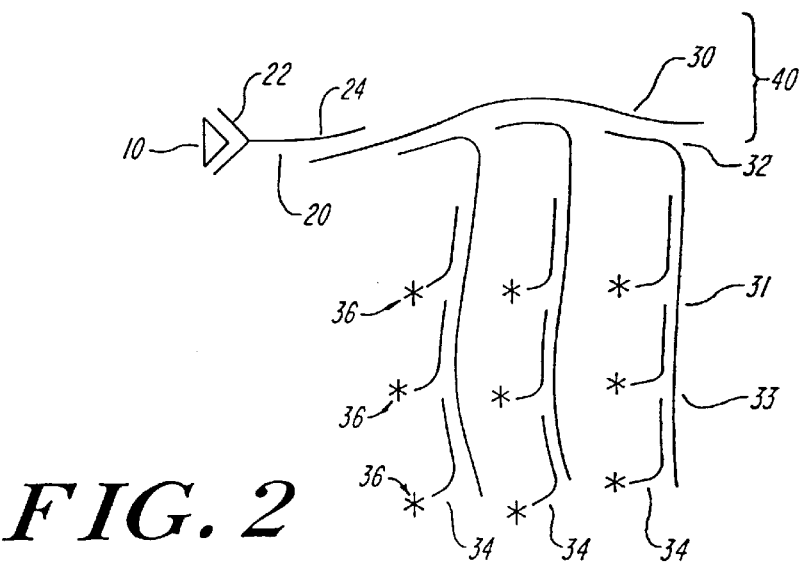
FIG. 2 depicts another embodiment of a detection method according to the invention.

It will further be appreciated that the signal can be amplified even further by providing additional binding sites for signalling moieties. Such a result can be obtained by "extending" the (first) amplifying entity with additional (second, third, etc.) amplifying entities which provide a greater number of binding sites for signalling moieties. For example, as shown in FIG. 2, the analyte:reagent:(first) amplifying entity complex 40 (in which the analyte 10 is illustrated as an antigen, which is recognized by antibody first portion 22 of the reagent 20) can be contacted with an extension reagent 31 which includes a first portion 32 which includes a polynucleotide sequence complementary to the (first) amplifying entity, but also includes a second portion 33 which comprises a polynucleotide portion to which a plurality of signalling moieties can bind. The second portion 33 of the extension reagent may include the same polynucleotide sequence as the second portion of the amplifying entity, or, preferably, can be different. Binding of the extension reagent 31 to the complex 40 results in formation of an "extended" complex. The "extended" complex can then be contacted with a plurality of signalling moieties 34, which include a detectable label and a polynucleotide sequence complementary to the second portion of the extension reagent 31, to detect the analyte. An example of reagent 31 suitable for use with a poly(dA) amplifying entity 30 is a poly(dT)-poly(dC) strand (prepared as described in Example 1, infra); the poly(dt) portion binds to the poly(da) strand, while the poly(dC) portion serves as a second RP to which a plurality of signalling moieties, such as $(dG)_{14}$-FITC can bind.

Figure 3:
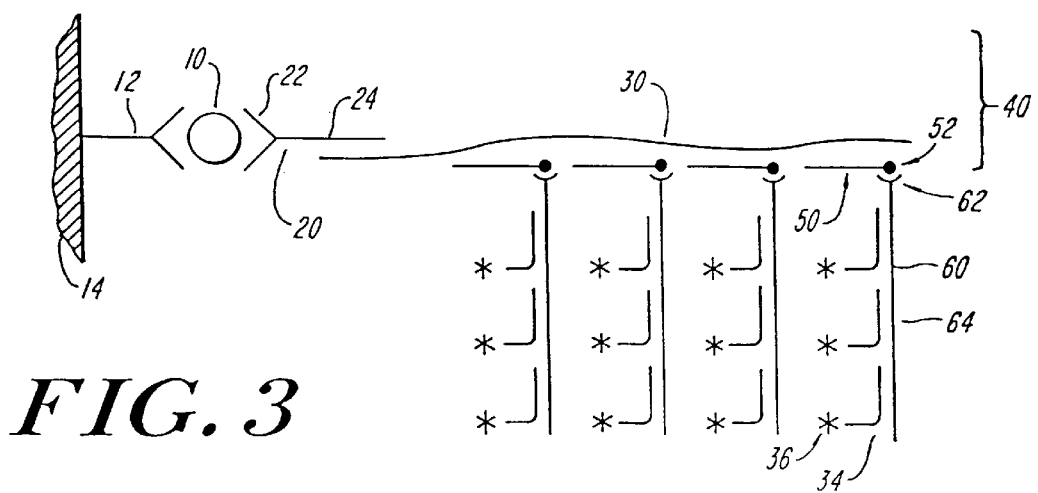
FIG. 3 shows another embodiment of a detection method according to the invention in which a second amplified is employed.

Additional binding sites for signalling moieties can be provided as shown in FIG. 3, in which the analyte 10 is depicted as an antigen which is immobilized on solid support 14 by a capture reagent 12 (e.g., a bound antibody). The steps of contacting the analyte with an analyte-complementary reagent to form an analyte:reagent complex, and contacting the analyte:reagent complex with a first amplifying entity to form an analyte:reagent:first-amplifying-entity complex, can be performed, e.g., as described hereinabove. In FIG. 3, the analyte:reagent:first-amplifying-entity 40 is contacted with a bifunctional reagent 50. The bifunctional reagent 50 includes a first portion which includes a polynucleotide sequence complementary to the second polynucleotide sequence of the first amplifying entity, and a second portion 52 which can be specifically recognized and bound by an extension reagent 60. An example of second portion 52 is a member of a specific-binding pair, e.g., as described herein. A preferred portion 52 is biotin. Extension reagent 60 includes a first portion 62 (e.g., streptavidin) which is capable of binding to portion 52 of the bifunctional reagent 50, and a second portion 64 which comprises a polynucleotide sequence to which a plurality of signalling moieties can bind. A plurality of signalling moieties 34 can bind to the second portion 64 as described herein to provide a signal which indicates the presence of the analyte 10 in the sample.

Thus, in another embodiment, the invention provides a method for detecting the presence or absence of an analyte in a sample, including the steps of contacting the sample with a first reagent having a first portion which specifically binds to the analyte and a second portion comprising a polynucleotide sequence, such that a complex of the analyte and the first reagent is formed; contacting the complex of the analyte and the first reagent with an amplifying entity having a first polynucleotide sequence and a second polynucleotide sequence, wherein the first polynucleotide sequence is complementary to the polynucleotide sequence of the second portion of the first reagent, such that a complex of the analyte, the first reagent, and the amplifying entity is formed; contacting the complex of the analyte, the first reagent, and the amplifying entity with a second reagent, the second reagent having a first portion which includes a polynucleotide sequence complementary to the second polynucleotide sequence of the amplifying entity, and a second portion, to form an extendable complex of the analyte, the first reagent, the amplifying entity and the second reagent; contacting the extendable complex with an extension reagent, the extension reagent comprising a first portion capable of specifically binding to the second portion of the amplifying entity, and a second portion which comprises a polynucleotide sequence, such that the extension reagent binds to the extendable complex to form a complex of the analyte, the first reagent, the amplifying entity, and the extension reagent; and contacting the complex of the analyte, the first reagent, the amplifying entity and the extension reagent with a plurality of signalling moieties, each of the signalling moieties comprising a detectable label and a polynucleotide sequence complementary to the polynucleotide sequence of the extension reagent, to form a detectable complex of the analyte, the reagent, the amplifying polynucleotide, the extension reagent and the signalling moieties; and detecting the label as indicative of the presence or absence of analyte in the sample.

In a preferred embodiment, the second portion of the bifunctional reagent comprises biotin, and the extension reagent first portion comprises streptavidin. In certain preferred embodiments, the first amplifying entity and the second amplifying entity do not include the same subsequence, to avoid non-specific binding. Thus, in an embodiment in which the first amplifying entity is poly(dA), the extension reagent second portion preferably comprises a different homopolynucleotide, preferably poly(dC). In an embodiment in which the second amplifying entity is poly(dC), each of the detectably-labeled signalling moieties preferably comprises poly(dG).

It will be appreciated that by appropriate selection of bifunctional reagents and additional amplifying entities, complexes which include several "layers" of amplifying entities can be formed, multiplying the number of signalling moieties which can bind to the complex and increasing the signal. However, it will be understood that as the number of amplifying entities is increased, the background "noise" generally increases.

II. Kits

In another aspect, the invention provides kits for the detection of an analyte in the sample.

In one embodiment, a kit comprises a container including a reagent having a first portion which specifically binds to the analyte and a second portion comprising a polynucleotide sequence; a container including an amplifying entity having a first polynucleotide sequence and a second polynucleotide sequence, wherein the first polynucleotide sequence is complementary to the polynucleotide sequence of the second portion of the reagent; a container including a plurality of signalling moieties, each of the signalling moieties comprising a detectable label and a polynucleotide sequence complementary to the second polynucleotide sequence of the amplifying entity; and instructions for detecting the presence or absence of the analyte in a sample. In a preferred embodiment, the amplifying entity is a homopolynucleotide, more preferably poly(dA), which preferably has a length of at least about 3000 bases, more preferably at least about 5000 bases, more preferably at least about 7000 bases, and still more preferably at least about 9000 bases.

In a preferred embodiment, the kit further comprises a container of an analyte-specific capture moiety. The analyte-specific capture moiety can be immobilized on a surface of, e.g., a container (e.g., a surface of the container of the analyte-specific capture moiety), which can optionally be a reaction vessel such as a 96-well plate. Alternatively, the analyte-specific capture moiety can be immobilized on the surface of a particle such as a bead, e.g., a magnetic microbead.

III. Compositions

In another aspect, the invention provides compounds and detectable complexes useful for detecting the presence or absence of an analyte in a sample.

In one embodiment, the invention provides the detectable complexes described hereinabove. In one embodiment, the invention provides a complex which includes a reagent which can bind to an analyte, the reagent having a first portion which specifically binds to the analyte and a second portion comprising a polynucleotide sequence; an amplifying entity bound to the reagent, the amplifying entity having a first polynucleotide sequence and a second polynucleotide sequence, wherein the first polynucleotide sequence is complementary to the polynucleotide sequence of the second portion of the reagent; and a plurality of signalling moieties bound to the amplifying entity, each of the signalling moieties comprising a detectable label and a polynucleotide sequence complementary to the second polynucleotide sequence of the amplifying entity. The complex can be formed in the presence or absence of analyte; if formed in the absence of the analyte, the complex can be contacted with a sample suspected of containing the analyte to detect the presence or absence of the analyte. In certain embodiments, the complex includes at least about 50 signalling moieties, more preferably at least about 100 signalling moieties, at least about 200 signalling moieties, or at least about 1000 signalling moieties. In certain embodiments, the complex includes the analyte, and the reagent first portion is bound to the analyte.

In another aspect, the invention provides homopolynucleotides useful a amplification entities. In one embodiment, the invention provides an isolated purified single-stranded homopolynucleotide having a length of at least about 3000 bases. In preferred embodiments, the homopolynucleotide has a length of at least about 7000 bases. In certain embodiments, the homopolynucleotide is selected from the group consisting of poly(dA), poly(dT), poly(dC), poly(dG), and poly(dU), most preferably poly(dA).

The following examples are intended to illustrate, but not to limit, the methods and compositions of the invention.

EXAMPLE 1

Long poly(dA) was prepared by a modification of a published procedure (*Methods in Molecular Biology*, Vol. 16, Ch. 7, pp. 95–105 (1993)). Terminal deoxyribonucleotidyl sransferase (TDT, EC 2.7.7.31)) was used to extend poly(da) purchased from Sigma Chemical Co. (St. Louis, Mo.). The literature procedure was modified by, inter alia, addition of excess TDT to improve the reaction time and/or yield of lengthened poly(dA).

A poly(da) solution was provided by dissolving poly(dA) in deionized water to a concentration which provided 12.5 $A_{260}$ units/ml. A solution of DATP in deionized water (concentration of 100 mM) was also prepared and frozen until use.

In a 1.5 ml microcentrifuge tube, the following reagents were combined:
  100 ul poly(da)
  200 ul 5× buffer (500 mM cacodylate pH 6.8, 5 mM $CoCl_2$, 0.5 mM DTT)
  20 ul DATP solution
  660 ul deinonized water
  750 units TDT
The reaction mixture was incubated overnight at 37° C.

The reaction mixture was purified with a buffer exchange column, eluted with deionized water, and further purified (e.g., to remove remaining excess ATP) by ultrafiltration with a Centricon 100 centifuge filter (Amicon, Beverly Mass.). The above extension procedure could be repeated to further extend the poly(dA).

An agarose gel analysis showed that the poly(da) before lengthening had an average length of about 1600–1650 bases. After one cycle of lengthening, the average length of the poly(da) strand was about 5000 bases; after two cycles, about 7000 bases; after three cycles, about 9000 bases. Further cycles of lengthening appeared to provide only minimal increases in strand length.

A similar procedure for lengthening poly(dC) was performed to provide longer poly(dC) sequences. To provide a hybrid reagent, a poly(dT) strand was successfully extended with dC bases in an analogous reaction.

EXAMPLE 2

The ability of poly(da) to bind to a signalling moiety was tested using FITC-$T_{20}$ and FITC-$T_{40}$ conjugates. Spectrophotometric analysis (260 nm) of the binding of the signalling moiety to poly(dA), in the absence of other components, showed that commercially-available poly(da) (Sigma), with a length of about 1650 bases per strand, bound about 282 FITC-$T_{20}$ moieties or about 93 FITC-$T_{40}$ moieties per strand of poly(dA) at room temperature. This is in excess of the maximum number of signalling moieties which could bind to the poly(dA) in a linear manner; the reason for the discrepancy is not fully understood.

Binding of signalling moieties to a sample of lengthened poly(da) with an average length of about 8000 bases per strand (prepared as in Example 1) was performed as described above. The results indicated that about 1100 FITC-$T_{20}$ moieties or about 484 FITC-$T_{40}$ moieties bound per strand of poly(da) at room temperature. Again, this is in excess of the maximum number of signalling moieties which could bind in a linear manner to the poly(dA).

It can be seen that, as expected, the lengthened poly(da) prepared in Example 1 provides a greater number of binding sites for signalling moieties than does commercially-available poly(dA).

EXAMPLE 3

An analyte-specific reagent for detection of human IgG was prepared as described below. The reagent included an anti-IgG portion and a poly(dT) "tail".

Goat anti-human IgG (available from Sigma Chemical Co., St. Louis. Mo.) in 5 mM EDTA was reduced with 2-mercaptoethylamine hydrochloride (MEA, Pierce, Rockford, Ill.) in buffer A (100 mM sodium phosphate, 5 mM EDTA, pH 6.0) to cleave the disulfide bond between the F(ab) fragments and provide a free sulfhydryl group. When reaction was complete (incubation was at 37° C. for 90 minutes), the mixture was diluted with sterile buffer B (20 mM sodium phosphate, 150 mM NaCl, 1 mM EDTA, pH 7.4) and purified on a Bio-Rad Econo-Pac 10DG column, eluting with Buffer B. Fractions were collected and assayed for protein with a BCA assay (BCA Protein Assay Reagent kit, Pierce)being careful to distinguish false positives due to the reducing reagent (MEA). The protein-containing fractions were pooled and the yield was calculated. An assay for determination of free sulfhydryl groups (Ellman's reagent) indicated that each antibody fragment may have several sulfhydryl groups. (However, some of these free sulfhydryl groups may not react with the modified DNA in the derivatization step, infra.)

3'-terminal amine-modified $(dT)_{35}$ was obtained from Oligos Inc., and treated with sulfo-succinimidyl-4-(N-maleimidomethyl)cyclohexane-1-carboxylate (Sulfo-SMCC, Pierce, 25 mole equiv.) in sterile PBS (20 mM sodium phosphate, 150 mM NaCl, pH 7.2) to derivatize the (dT)$_{35}$ amino group. The reaction was typically incubated for 60 minutes at room temperature or for 30 minutes at 37° C. The derivatized (dT)$_{35}$ was purified (on a Bio-Rad Econ-Pac column eluting with Buffer B). Fractions containing modified DNA were detected by measuring the UV absorbance at 260 nm. The derivatized DNA was then conjugated to the cleaved F(ab) fragments prepared from anti-human IgG (molar ration of modified DNA to protein was 10:1) by incubation for at least 2 hours at 4° C. (or overnight). The conjugate was purified with a Centricon 60 centrifuge filter (Amicon) to provide the analyte-specific reagent.

Other protein conjugates were derivatized with a (dT)$_{35}$ tail according to this procedure with only minor changes. Thus, analyte-specific reagents were prepared from polyclonal antibodies (goat anti-human IgG, goat anti-mouse IgG, and sheep anti-rabbit IgG), monoclonal antibodies (mouse monoclonal anti-FITC, mouse monoclonal antibiotin), and other proteins (streptavidin and alkaline phosphatase (AP)).

EXAMPLE 4

The following protocol was used for this example:

1 pmol of the capture hairpin was incubated with the appropriate target in 100 microliters of reaction buffer (100 mM Tris-HCl, 1 M NaCl, 0.08% Triton-X-100, pH 8) per well. The reaction was heated to 95° C. for 5 minutes and then cooled to room temperature. The reaction mixture was loaded into high-capacity streptavidin-coated microtiter plates (available from, e.g., Boehringer Mannheim) and incubated 45 minutes. The wells were washed 6× with reaction buffer.

For direct detection, the protocol described at "Signal generation," below, was then followed. For amplified reactions, a secondary probe molecule (a T$_{20}$-tailed polynucleotide complementary to a target sequence) was suspended in reaction buffer at a concentration of 100 pmol per 100 microliters of reaction buffer. The target mixture was loaded into wells and incubated for 45 minutes. A poly(dA) solution (250 ng/100 microliters reaction buffer) was then added (100 microliters) to each well and incubated for 45 minutes. The wells were washed 6x with reaction buffer.

A solution of signal moiety (FITC-T$_{15}$-FITC) was dissolved in reaction buffer (4 pmol signal/100 microliters buffer). The signal solution was loaded into wells, incubated 45 minutes, and then washed 6× with reaction buffer, followed by signal generation.

Signal generation:

The anti-FITC/alkaline phosphatase conjugate was diluted 6000-fold in Tris-buffered saline (150 mM NaCl, 20 mM Tris, pH 8), and 100 microliters was loaded into each well and incubated for 45 minutes. The wells were washed 6× with ⅒-strength reaction buffer. The alkaline phosphatase substrate was added, the color developed, and the results were read by a plate reader.

In this example, a synthetic target molecule was employed as analyte. The target was custom synthesized by and purchased from Oligo Therapeutics (Wilsonville, Oreg.), and had the following sequence:

5'-FITC-AC AAG CGG CTA GGA GTT CCG CAG TAT GGA TCG GCA GAG GAG CCt3' (SEQ ID NO: 1)

The presence of the FITC moiety did not prevent the analyte from binding to the capture hairpin probe or to the detector moiety. The analyte was captured by an immobilized hairpin probe having the following sequence 5'-CTAGT CGACG TGGTC CTTU$_B$T TGGAC CACGT CGACT AG GGCTC CTCTG CCGAT CCATA-3 (SEQ ID NO: 2)

in which U$_B$ indicates a biotinylated uracil through which the hairpin was immobilized to a streptavidin-coated plate. The secondary probe had the following sequence:

5'-CTG CGG AAC TCC TAG CCG CTT GTT TTTTT TTTTT TTTTT-3' (SEQ ID NO: 3).

Figure 4A:
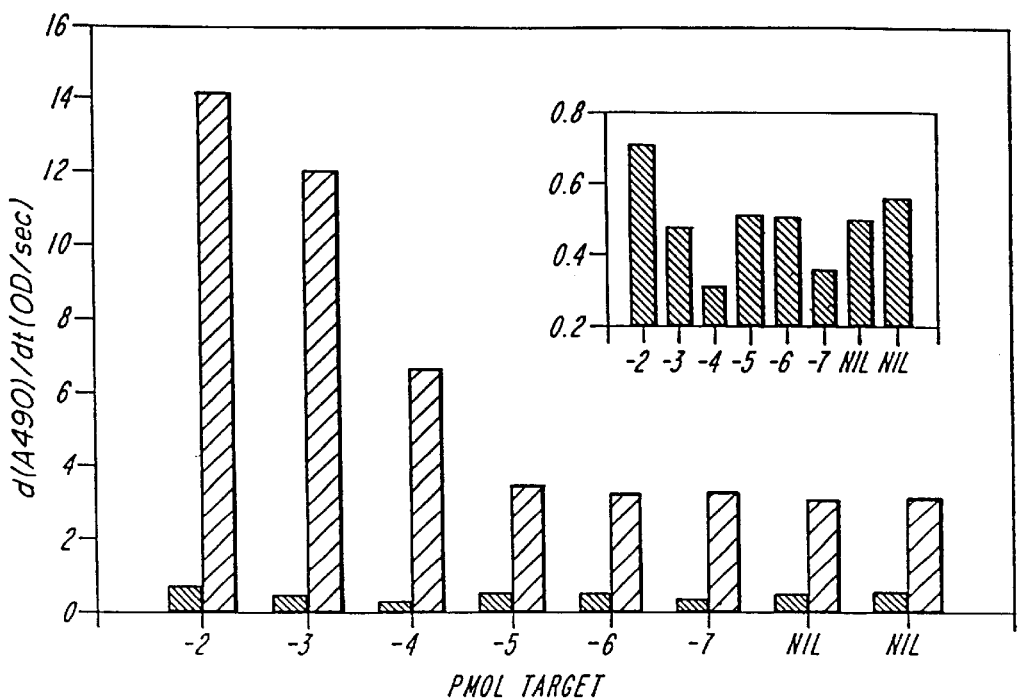
FIGS. 4A and 4B are bar graphs comparing a detection method of the invention to direct detection of a nucleic acid sequence.
Figure 4B:
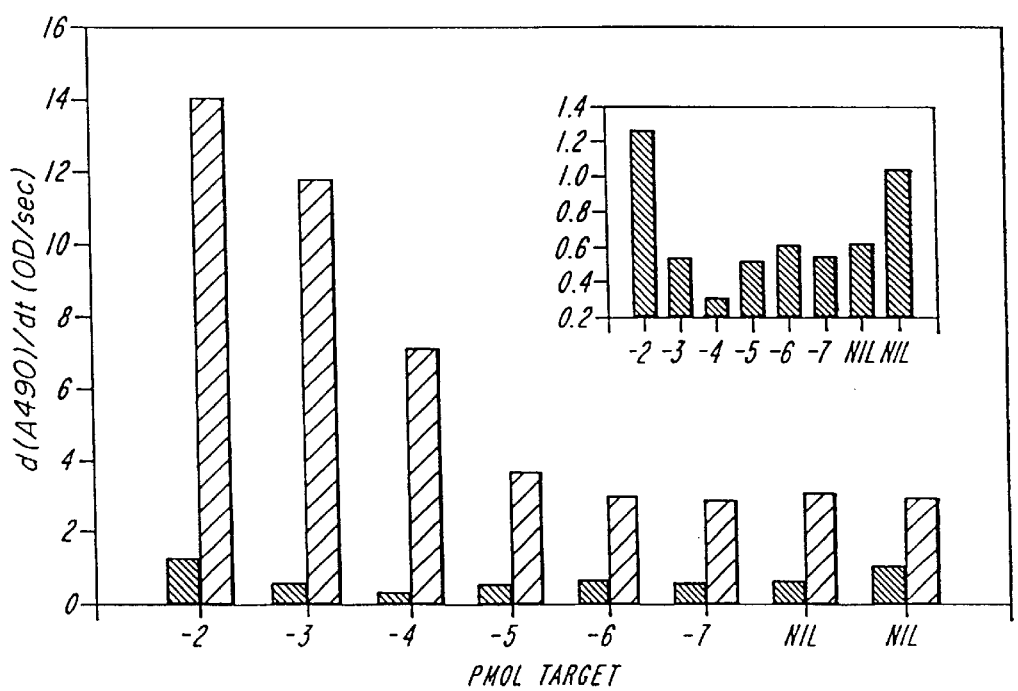

FIG. 4 shows a comparison of direct and amplified DNA detection. In FIG. 4, the gray bars represent direct detection of DNA, while the black bars represent detection according to the method of the invention The inset shows an expanded scale for the direct detection data. The vertical axis is in units corresponding to the change in absorbance (OD) per unit time(seconds); this slope was more readily determined with our plate reader than a fixed OD reading.

According to FIG. 4, the amplified DNA detection system provided more signal than did the direct detection scheme (however, the amplified system also had greater noise, as seen by the larger signal when no analyte was present (columns labelled "nil")). The amplified system detected analyte at levels as low as 10$^{-4}$ pmol (signal greater than baseline noise level). In contrast, direct detection was unable to detect levels of analyte below 10$^{-2}$ pmol (signal level not above background).

EXAMPLE 5

A model antibody-based amplification system was prepared and compared to a direct detection scheme.

Microtiter plates were coated with human IgG (Sigma) at concentrations from 50 ng to 50 fg per well. Control wells (labelled "nil" in FIG. 5) had no IgG. The presence of IgG on the plates was then detected with either an anti-IgG/alkaline phosphatase (AP) conjugate (Sigma) with calorimetric detection, or with the anti-IgG/poly(dT) conjugate prepared in Example 3, supra, with amplified detection.

Figure 5A:
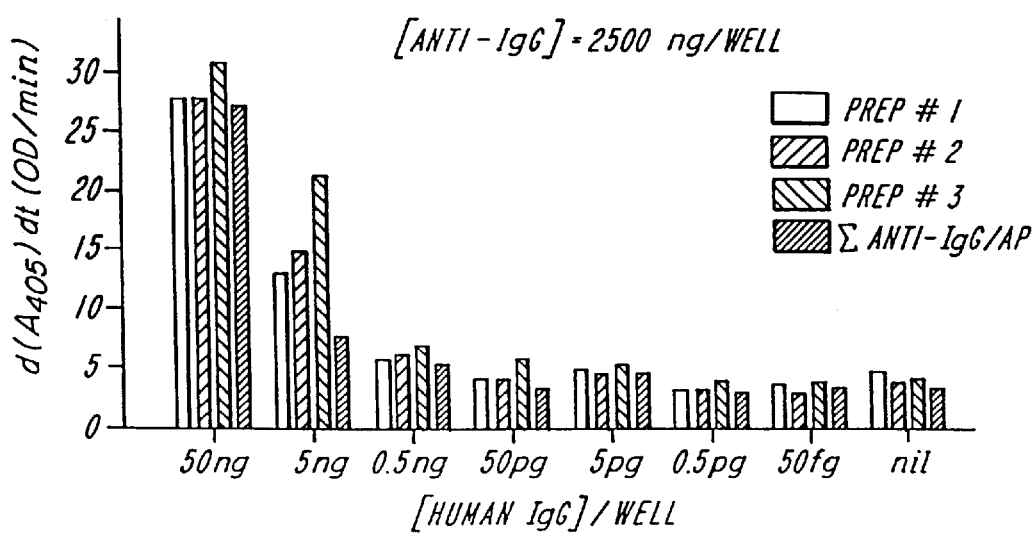
FIGS. 5A–5C depict an ELISA with signal amplification according to the invention.
Figure 5B:
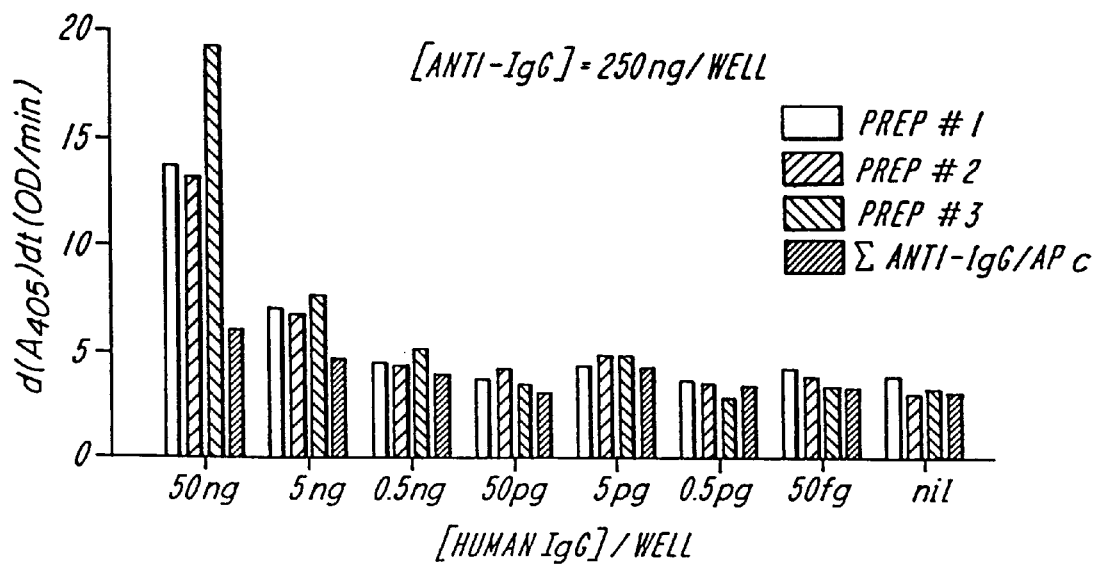
Figure 5C:
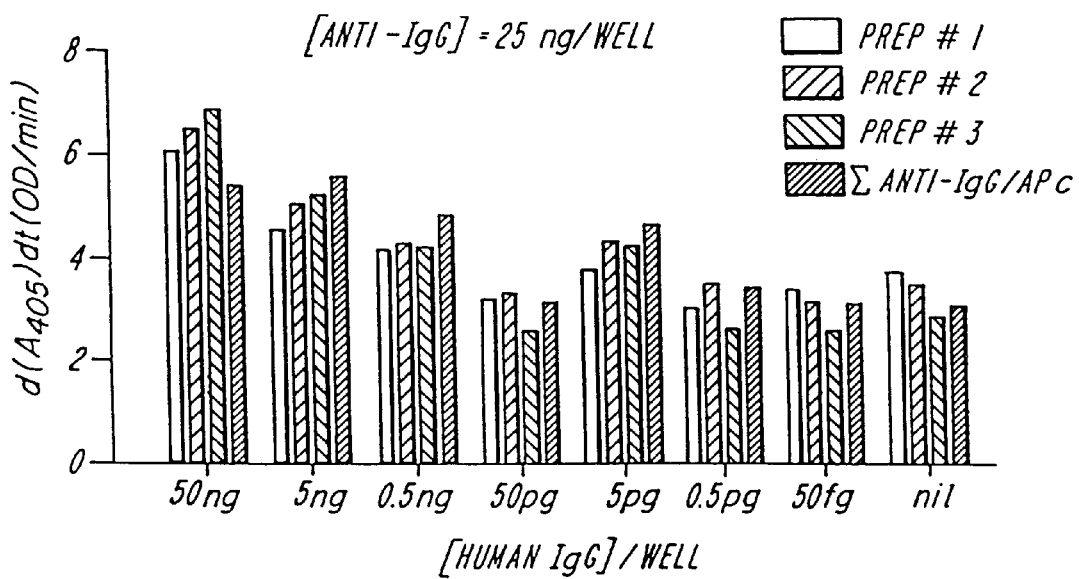

The results are shown in FIG. 5. The test bars (Prep #1, Prep #2 and Prep #3) represent the results of assays using three different preparations of the anti-IgG/poly(dT) reagent described in Example 3. The black bar represents assays using a conventional (Sigma) anti-IgG/alkaline phosphatase (AP) reagent for signal generation. The different panels were obtained using the concentration of anti-IgG reagent (either anti-IgG/poly(dT) or anti-IgG/AP) indicated in the inset caption. The vertical axis is change in optical density (OD) per second. The horizontal line corresponds to the signal level generated by direct detection in the control sample.

FIG. 5 shows the three preparations of anti-IgG/poly(dT) reagent generally gave similar results, although Prep #3 generated the largest signal. The amplified detection method provided greater signal in this model system than the direct detection at high concentrations of immobilized IgG. At anti-IgG concentration of 25 ng/well, the amplified reaction had a detection limit similar to direct detection, while at anti-IgG concentrations of 250 or 2500 ng/well, the amplified detection system was similar to or more sensitive than direct detection of IgG.

EXAMPLE 6

A comparison of direct detection with two amplifications according to the present invention was performed, using biotin as a sample analyte.

Nunc Maxisorp sample plates (Nunc, Inc.) were coated with BSA-biotin (Sigma) to provide a biotin-coated surface.

The concentration of BSA-biotin was varied in 10-fold increments to provide plates having varying amounts of BSA-biotin analyte immobilized on the surface; the lowest amount loaded was 0.01 pg, up to a maximum of 1000 pg. Control plates had no biotin analyte immobilized on the surface.

"Direct" detection was performed using a streptavidin-horse radish peroxidase (HRP) conjugate (available from, e.g., Sigma) to bind to immobilized biotin; colorimetric detection of bound HRP was performed according to a standard protocol.

Amplification (referred to in FIG. 6 as "1× amplification") was accomplished by contacting the plate with streptavidin (0.05 pmol), followed by washing and addition of a biotin-$dT_{30}$ conjugate (purchased from Oligos) (1 pmol) to bind to the bound streptavidin. Lengthened poly(da) (produced as in Example 1) was then added (5 ng), followed by a FITC-$T_{20}$-FITC signalling moiety (available from Oligos). The presence of signalling moiety was detected with an anti-FITC/biotin conjugate (Sigma) (0.25 pmol), followed by streptavidin-HRP conjugate with colorimetric detection of HRP as above. (An alternate detection scheme used biotin-$T_{30}$ conjugate signalling moieties to hybridize to the poly (dA), followed by addition of streptavidin-HRP conjugate to detect the signalling moieties.)

Amplification with an extension reagent (referred to in FIG. 6 as "2× amplification") was performed by contacting the plate sequentially with streptavidin, biotin-$T_{30}$ conjugate and poly(da) as described above. Biotin-$T_{30}$ conjugate was then added as an extension reagent (to bind to the poly(dA)). This complex was then extended by addition of streptavidin (0.05 pmol) to bind to the biotinylated extension reagent, followed by biotin-$T_{30}$ conjugate, then poly(dA) (5 ng). FITC-$T_{20}$-FITC signalling moiety was then added and detected as described above.

Figure 6:
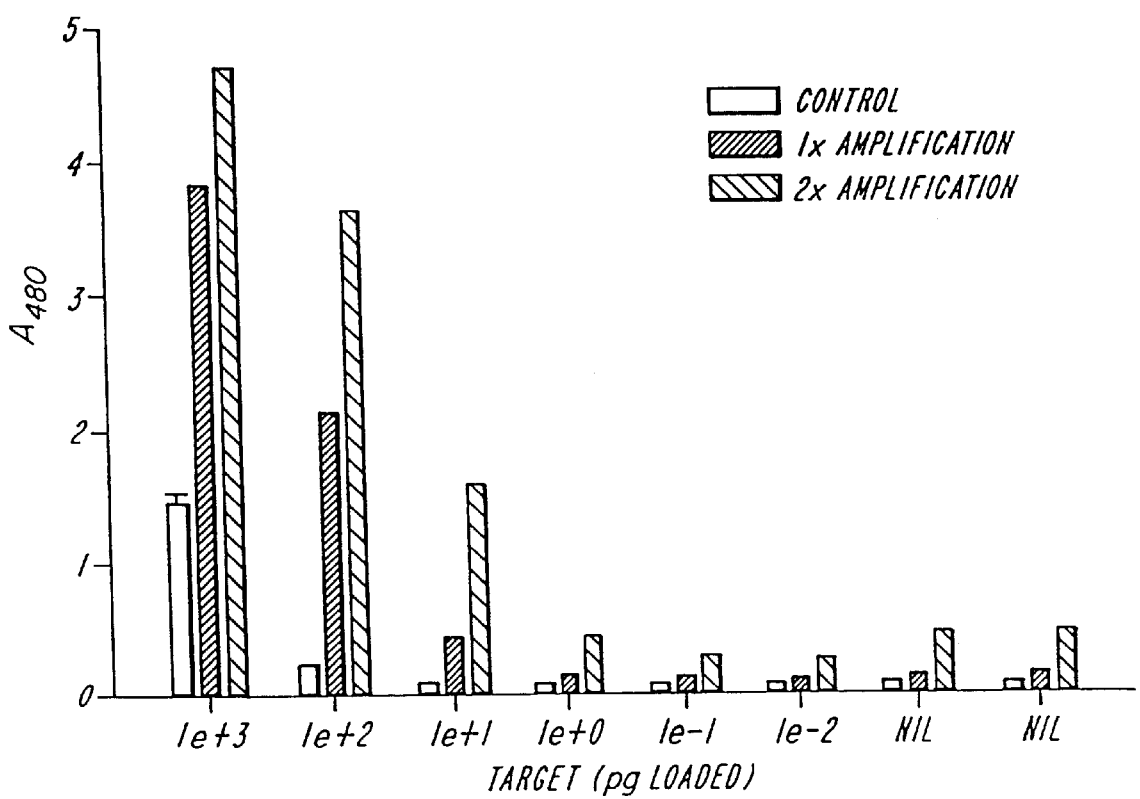
FIG. 6 graphically depicts the results an HIV p24 assay according to the invention.

The results of the assays are shown in FIG. 6. "Direct" detection is labeled as "Control" in FIG. 6; plates with no biotin analyte are labeled "Nil". It can be seen that both amplification methods provided greater signal intensities than the direct detection method; the extended amplification scheme generally provided the greatest signal. However, the amplification methods did result in greater "noise" than direct detection, as seen by comparison of the "nil" (no analyte) assay results. Despite the increased noise, the amplification methods provided greater signal-to-noise ratios at lower concentrations. The signal with direct detection dropped to background levels below 100 pg loading of analyte, while both amplification methods provided signal above background at 1 pg analyte loading. The amplification methods thus appear to provide a 10–100 fold increase in detection sensitivity in this system.

An alternative form of extension amplification, using a $(dT)_{20}$-poly(dC) strand (about 500–700 dC bases were tailed onto the $dT_{20}$) as both extension reagent and second amplification entity, and $(dG)_{14}$-FITC as signalling moieties, was found to provide generally similar results.

EXAMPLE 7

Human immunodeficiency virus (HIV) infection can be diagnosed with an antibody-based reaction system based on the presence of the p24 antigen of HIV in blood. In this example, a "direct" detection system was compared with an amplified detection system.

Wells of a reaction plate were coated with commercially-available anti-p24 antibody (available in a kit from Dupont, Boston, Mass.). Samples containing varying levels of p24 antibody were added to the wells (a control well had no antigen), followed by addition of a biotinylated polyclonal anti-p24 antibody (Dupont, Boston, Mass.). The "direct" detection of p24 antigen was performed by addition of streptavidin-HRP conjugate and colorimetric detection with an HRP substrate (OPD, provided with the Dupont kit). Amplified detection was performed by addition of streptavidin-$T_{35}$ conjugate, followed by poly(dA), then biotin-$T_{30}$ conjugate, and finally streptavidin-HRP conjugate, with calorimetric detection as above.

The results showed that the amplified detection system was able to detect the presence of p24 at levels at least 10-fold lower than the direct detection system.

Those skilled in the art will recognize, or be able to ascertain using no more than routine experimentation, numerous equivalents to the specific procedures described herein. Such equivalents are considered to be within the scope of this invention and are covered by the following claims.

The contents of all references and patent applications cited herein are hereby incorporated by reference.

What is claimed is:

1. A method for detecting the presence or absence of an analyte in a sample, the method comprising:
   contacting the sample with a reagent having a first portion which specifically binds to the analyte and a second portion comprising a polynucleotide sequence, such that a complex of the analyte and the reagent is formed;
   contacting the complex of the analyte and the reagent with an amplifying entity which is a homopolynucleotide having a first polynucleotide sequence and a second polynucleotide sequence, wherein the first polynucleotide sequence is complementary to the polynucleotide sequence of the second portion of the reagent, such that a complex of the analyte, the reagent, and the amplifying entity is formed;
   contacting the complex of the analyte, the reagent, and the amplifying entity with a plurality of signalling moieties, each of the signalling moieties comprising a detectable label and a polynucleotide sequence complementary to the second polynucleotide sequence of the amplifying entity, to form a detectable complex of the analyte, the reagent, the amplifying polynucleotide and the signalling moieties; and
   detecting the label as indicative of the presence or absence of analyte in the sample.

2. The method of claim 1, wherein the analyte is a nucleic acid sequence.

3. The method of claim 2, wherein the reagent first portion is a nucleic acid sequence which is complementary to the analyte.

4. The method of claim 1, wherein the analyte is an antibody or antigen.

5. The method of claim 4, wherein the reagent first portion is an antibody or antigen which specifically binds with the analyte.

6. The method of claim 1, wherein the amplifying entity first polynucleotide sequence and second polynucleotide sequence comprise the same sequence.

7. The method of claim 1, wherein the homopolynucleotide comprises poly(dA).

8. The method of claim 7, wherein the poly(dA) has a length of at least about 3000 bases.

9. The method of claim 7, wherein each of the signalling moieties comprises poly(dT).

10. The method of claim 7, wherein the reagent second portion comprises poly(dT).

11. The method of claim 1, wherein each of the plurality of signalling moieties comprises a detectable label selected from the group consisting of antigens, antibodies, enzymes, radioisotopes, and fluorescent moieties.

12. The method of claim 1, wherein, prior to the step of contacting the complex of the analyte, the reagent and the amplifying entity with the plurality of signalling moieties, the method comprises the further step of washing the complex of the analyte, the reagent and the amplifying entity to remove unbound polynucleotide.

13. The method of claim 1, wherein the analyte is immobilized with an immobilized capture reagent.

14. The method of claim 1, wherein the first polynucleotide sequence of the amplifying entity and the second polynucleotide sequence of the amplifying entity comprises the same sequence.

15. A method for detecting the presence or absence of an analyte in a sample, the method comprising:
   contacting the sample with a first reagent having a first portion which specifically binds to the analyte and a second portion comprising a polynucleotide sequence, such that a complex of the analyte and the first reagent is formed;
   contacting the complex of the analyte and the first reagent with an amplifying entity having a first polynucleotide sequence and a second polynucleotide sequence, wherein the first polynucleotide sequence is complementary to the polynucleotide sequence of the second portion of the first reagent, such that a complex of the analyte, the first reagent, and the amplifying entity is formed;
   contacting the complex of the analyte, the first reagent, and the amplifying entity with a second reagent, the second reagent having a first portion which includes a polynucleotide sequence complementary to the second polynucleotide sequence of the amplifying entity, and a second portion, to form an extendable complex of the analyte, the first reagent, the amplifying entity and the second reagent;
   contacting the extendable complex with an extension reagent, the extension reagent comprising a first portion capable of specifically binding to the second portion of the amplifying entity, and a second portion which comprises a polynucleotide sequence, such that the extension reagent binds to the extendable complex to form a complex of the analyte, the first reagent, the amplifying entity, and the extension reagent; and contacting the complex of the analyte, the first reagent, the amplifying entity and the extension reagent with a plurality of signalling moieties, each of the signalling moieties comprising a detectable label and a polynucleotide sequence complementary to the polynucleotide sequence of the extension reagent, to form a detectable complex of the analyte, the reagent, the amplifying polynucleotide, the extension reagent and the signalling moieties; and detecting the label as indicative of the presence or absence of analyte in the sample.

16. The method of claim 15, wherein the second portion of the extension reagent comprises a homopolynucleotide.

17. The method of claim 16, wherein the second portion of the extension reagent comprises poly(dC), and the polynucleotide sequence of the signalling moieties comprises poly(dG).

18. The method of claim 17, wherein the detectable label is selected from the group consisting of antigens, antibolies, enzymes, radioisotopes, and fluorescent moieties.

19. A kit for detecting the presence or absence of an analyte in a sample, the kit comprising:

a container including a reagent having a first portion which specifically binds to the analyte and a second portion comprising a polynucleotide sequence;

a container including an amplifying entity which is a homopolynucleotide having a first polynucleotide sequence and a second polynucleotide sequence, wherein the first polynucleotide sequence is complementary to the polynucleotide sequence of the second portion of the reagent;

a container including a plurality of signalling moieties, each of the signalling moieties comprising a detectable label and a polynucleotide sequence complementary to the second polynucleotide sequence of the amplifying entity; and instructions for detecting the presence or absence of the analyte in a sample.

20. The kit of claim 19, wherein the homopolynucleotide comprises poly(dA).

21. The kit of claim 20, wherein the poly(dA) has a length of at least about 3000 bases.

22. The kit of claim 20, wherein the reagent second portion comprises poly(dT).

23. The kit of claim 19, further comprising a container of an analyte-specific capture reagent.

24. The kit of claim 23, wherein the analyte-specific capture reagent is immobilized on a solid support.

25. A detectable complex for detection of an analyte, the complex comprising:

an analyte;

a reagent bound to the analyte, the reagent having a first portion which specifically binds to the analyte and a second portion comprising a polynucleotide sequence;

an amplifying entity which is a homopolynucleotide bound to the reagent, the amplifying entity having a first polynucleotide sequence and a second polynucleotide sequence, wherein the first polynucleotide sequence is complementary to the polynucleotide sequence of the second portion of the reagent; and a plurality of signalling moieties bound to the amplifying entity, each of the signalling moieties comprising a detectable label and a polynucleotide sequence complementary to the second polynucleotide sequence of the amplifying entity.

26. The detectable complex of claim 25, further comprising an analyte-specific capture reagent bound to a solid support, the capture reagent further being bound to the analyte.

27. The detectable complex of claim 26, wherein the analyte is an antigen.

28. The detectable complex of claim 26, wherein the analyte is a nucleic acid.

29. An isolated purified single-stranded homopolynucleotide having a length of at least about 3000 bases.

30. The homopolynucleotide of claim 29, wherein the homopolynucleotide has a length of at least about 7000 bases.

31. The homopolynucleotide of claim 29, wherein the homopolynucleotide is selected from the group consisting of poly(dA), poly(dT), poly(dC), poly(dG), and poly(dU).

* * * * *